United States Patent [19]

Boger et al.

[11] Patent Number: 4,705,892
[45] Date of Patent: Nov. 10, 1987

[54] PROCESS FOR PREPARING ALPHA,OMEGA-DIAMINO ACIDS

[75] Inventors: Joshua S. Boger, Westfield, N.J.; Linda S. Payne, Lansdale, Pa.

[73] Assignee: Merck & Co., Inc., Rahway, N.Y.

[21] Appl. No.: 915,829

[22] Filed: Oct. 16, 1986

Related U.S. Application Data

[63] Continuation-in-part of Ser. No. 736,733, May 22, 1985, abandoned.

[51] Int. Cl.$^4$ ............................................. C07C 101/24
[52] U.S. Cl. ................................... 562/562; 548/473; 548/477; 548/478; 560/163; 562/561
[58] Field of Search ................. 548/478, 473, 477; 562/561, 562

[56] References Cited

U.S. PATENT DOCUMENTS

| | | | |
|---|---|---|---|
| 3,637,838 | 1/1972 | Tetenbaum | 548/477 |
| 4,003,862 | 1/1977 | Albright | 548/477 |
| 4,515,964 | 5/1985 | Boyer | 548/477 |

FOREIGN PATENT DOCUMENTS 277944  10/1964  Canada ................................ 548/478

OTHER PUBLICATIONS

Gaudry, Can. J. Chem., 31, pp. 1060–1063 (1953).
Richards, Can. J. Chem., 60, pp. 2810–2820 (1982).
Ault, "Techniques and Experiments for Organic Chemistry", 4th Ed., pp. 148–149 (1983).

Primary Examiner—Michael L. Shippen
Attorney, Agent, or Firm—Richard A. Edler; Hesna J. Pfeiffer

[57] ABSTRACT

An improved process for preparing $\alpha,\omega$-diamino acids, such as D,L-homolysine, 2,8-diaminooctanoic acid, ornithine, lysine, or the like, comprising reaction of phthalic anhydride and an amino alcohol in a hydrocarbon solvent; treatment of the resulting phthalimide—N—$(CH_2)_n$—OH derivative, without isolation thereof, with phosphorus tribromide or phosphorous pentachloride; alkylation of diethyl acetamidomalonate with the phthalimide—N—$(CH_2)_n$—chloride or —bromide of the previous step, in the presence of, particularly, sodium hydride/dimethylformamide; standard acid hydrolysis and decarboxylation; selective protection via copper(II) chelation, N-specific acylation with benzyl chloroformate, and decomposition of the amino acid-copper(II) complex with alkaline thioacetamide; standard t-butoxycarbonyl acylation; and deprotection to obtain the desired $\alpha,\omega$-diamino acids.

7 Claims, No Drawings

PROCESS FOR PREPARING ALPHA,OMEGA-DIAMINO ACIDS

BACKGROUND OF THE INVENTION

The instant application is a continuation-in-part of U.S. application Ser. No. 736,733, filed May 22, 1985 now abandoned.

The present invention concerns more efficient processes for preparing $\alpha,\omega$-diamino acids fo the formula:

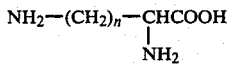

such as D,L-homolysine, 2,8-diaminooctanoic acid, ornithine, lysine, or the like, which particularly comprises in its first process step, the reaction of phthalic anhydride and an amino alcohol in a hydrocarbon solvent, such as toluene, benzene, xylene or a mixture thereof.

$\alpha,\omega$-Diamino acids have a myriad of uses, including, especially, as intermediates in the preparation of peptides or peptide-like compounds which are somatostatin analogs [see e.g. Nutt et al., *Int. J. Peptide Protein Res.*, 21, 66 (1983)], or which themselves have activity as angiotensin converting enzyme inhibitors [see e.g. Wu et al., *J. Pharm. Sci.*, 74 No. 3, 352 (1985)], or as renin inhibitors.

Procedures for preparing $\alpha,\omega$-diamino acids such as D.L-homolysine or D,L-ornithine are known [see e.g. Albertson et al., *J. Am. Chem. Soc.*, 67, 308 (1945); Takagi et al., *Chem. Pharm. Bull.*, 7, 1983 (1959); Kirret et al., *Eesti. NSV Tead. Akad. Toim. Keem. Geol.*, 19, 369 (1970); or R. Gaudry, *Can. J. Chem.*, 31, 1060 (1953)] but the yields of product is generally low ($\leq 20\%$). Further, the Gaudry reference warns against the formation of a two-phase reaction mixture upon the reaction of 3-aminopropanol with phthalic anhydride, from which would ensue a violent reaction upon the addition of phosphorous tribromide.

SUMMARY OF THE INVENTION

The instant invention is directed to an improved process for preparing $\alpha,\omega$-diamino acids of the formula:

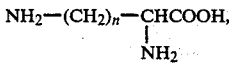

such as D,L-homolysine, 2,8-diaminooctanoic acid, ornithine, lysine, or the like, which comprises reaction of phthalic anhydride and an amino alcohol in a hydrocarbon solvent, such as toluene, benzene, xylene or a mixture thereof; treatment of the resulting phthalimide-N-(CH$_2$)$_n$-OH derivative, without isolation thereof, with phosphorous tribromide or phosphorous pentachloride; alkylation of diethyl acetamidomalonate with the phthalimide-N-(CH$_2$)$_n$-chloride or -bromide of the previous step, in the presence of, particularly, sodium hydride/dimethylformamide; standard acid hydrolysis and decarboxylation; selective protection via copper(II) chelatin, N-specific acylation with benzyl chloroformate, and decomposition of the amino acid-copper(II) complex with alkaline thioacetamide; standard t-butoxycarbonyl acylation; and deprotection to obtain the desired $\alpha,\omega$-diamino acids, which are especially useful, inter alia, as intermediates in the preparation of peptides of peptide-like compounds that are somatostatin analogs, or have activity as angiotensin converting enzyme inhibitors or as renin inhibitors.

DETAILED DESCRIPTION OF THE INVENTION

The invention comprises a process for preparing $\alpha,\omega$-diamino acids of the formula:

wherein n is 3-10, preferably 3-6, and most preferably 5-6, which comprises:

(a) reaction of phthalic anhydride and an amino alcohol of the formula:

in a hydrocarbon solvent, such as toluene, benzene, xylene or a mixture thereof, and the azeotropic removal of water formed in this reaction;

(b) treatment of the reaction product from step "a" (a phthalimide—N—(CH$_2$)$_n$—OH derivative), without isolation thereof, with phosphorous tribromide (PBr$_3$) or phosphorous pentachloride (PCl$_5$), to obtain:

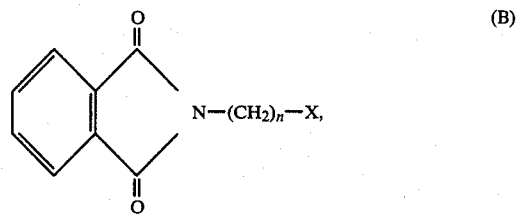

wherein X is Cl or Br;

(c) alkylating diethyl acetamidomalonate with the product of step "b", the compound of formula B in the presence of sodium hydride in dimethylformamide (NaH/DMF) or sodium ethoxide in ethanol (NaOC$_2$H$_5$/C$_2$H$_5$OH) to obtain:

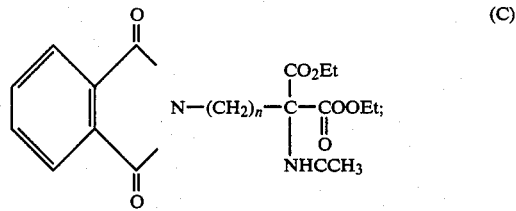

(d) hydrolyzing and decarboxylating the product of step "c", the compound of formula C to obtain:

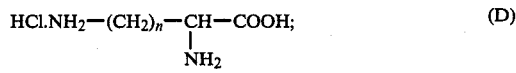

(e) chelating the product of step "d", the compound of formula D with CuCl$_2$, acylating the chelate with benzylchloroformate of the formula, Z—Cl, where Z is

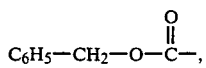

and decomposing the acylated chelate with alkaline thioacetamide of the formula,

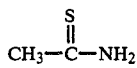

to obtain:

$$Z-NH-(CH_2)_n-CH-COOH; \quad (E)$$
$$\hspace{3.5cm} | $$
$$\hspace{3.5cm} NH_2$$

(f) acylating the product of step "e", the compound of formula E, to obtain the N-protected derivative of the formula:

$$ZNH-(CH_2)_n-CH-COOH, \quad (F)$$
$$\hspace{3cm} | $$
$$\hspace{3cm} NHL$$

wherein L is a urethane-type protecting group, such as tert-butyloxycarbonyl (t-Boc), benzyloxycarbonyl (Z), furfuryloxycarbonyl (Foc), diisopropylmethyloxycarboxyl (Dmc), or the like; and
(g) deprotecting the product of step f, the compound of formula F to obtain an α,ω-amino formula I.

The present invention also comprises the preparation of phthalimide—N—(CH$_2$)$_n$—OH derivatives according to step "a", above, by the reaction of phthalic anhydride and an amino alcohol in the presence of hydrocarbon solvent, such as toluene, benzene, xylene or mixtures therof, which promotes reaction homogeneity and allows the azeotropic removal of water formed during the reaction. By this improved process, the creation of a two-phase reaction mixture is averted, and when the phthalimide—N—(CH$_2$)$_n$—OH derivatives are reacted directly, without the extra step of isolation of these derivatives, with PX$_3$, the reaction is less violent and the yield of the phthalimide—N—(CH$_2$)$_n$—X derivative increased up to three fold.

The following set of reaction schemes illustrates the process of the present invention:

Reaction Scheme

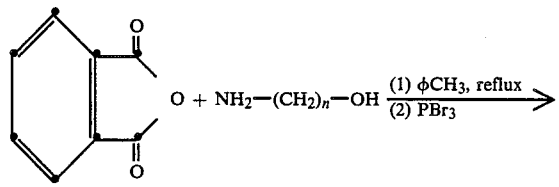

A = PHTHALIC ANHYDRIDE
1n = 5
2n = 6

-continued
Reaction Scheme

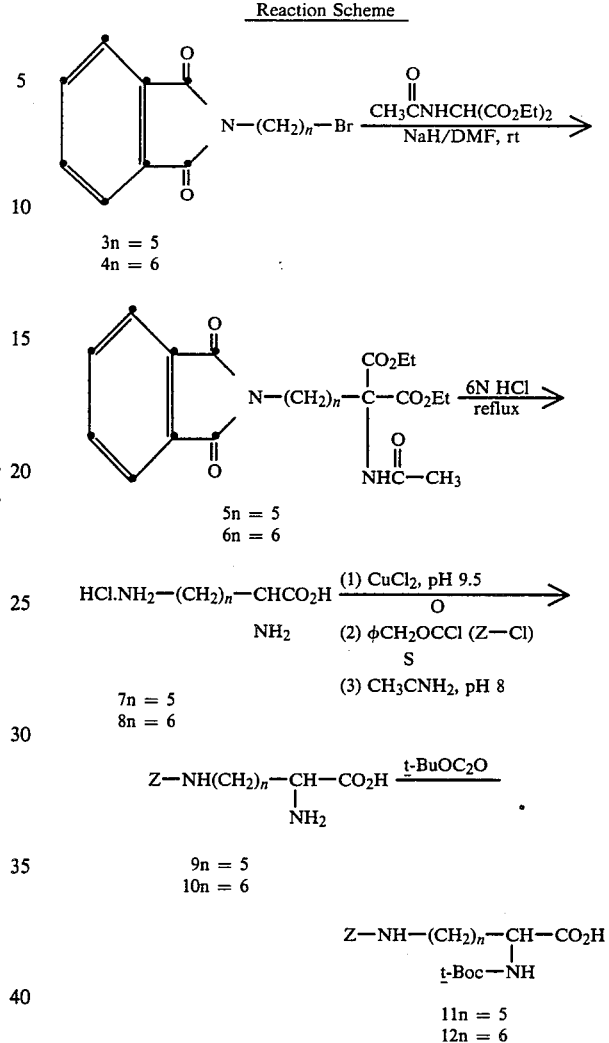

The initial reaction, phthalimide formation with aminoalcohol 1 or 2, in our modified acetamidomalonic ester approach, as shown in Scheme I, was significantly improved through the use of solvent, such as toluene, over Gaudry's neat conditions. The water which is formed during the course of this reaction is azeotropically removed, averting a two phase reaction mixture and the ensuing violent reaction upon addition of phosphorous tribromide. The intermediate 5-hydroxy-pentylphthalmide (reaction of A with 1 or 2) was not isolated, but treated with phosphorous tribromide directly to give 5-bromopentylphthalimide 3. Dehydration of the intermediate alcohol in a side reaction was estimated to be 5-10% based on TLC and $^1$H NMR.

In the key alkylation step, sodium hydride in dimethylformamide was substituted for sodium ethoxide in ethanol with significant improvement in the rate of reaction, as shown by the time to completion by TLC (18 h, 25° C. versus 48 h, 80° C.). The purity of the crude product, 5, improves significantly with this modification. Purification of diethyl 2-acetamido-2-(5-phthalimidopentyl)-malonate 5 prior to acid hydrolysis by a fast pass through a Still column [Still et al., *J. Org. Chem.*, 43, 2923 (1978)] afforded purified 5 in 78% yield.

Application of standard hydrolysis procedures (5 h, 6 N HCl, reflux) cleanly effected both hydrolysis and decarboxylation of 5. The hydrolysate was adsorbed on a strong cation exchange resin column, eluted with an ammonium hydroxide gradient and, following pH adjustment of the concentrated eluant, the monohydrochloride of D,L-homolysine 7 was isolated in 55% overall yield after three steps. The literature contains extraction workups for the isolation of diamino acids, but recovery and salt form vary, making isolation of crystalline product tedious.

A selective protection sequence via copper-II chelate complex of 7 allowed for N-specific acylation with benzyl chloroformate (Z—Cl) under Schotten-Baumann conditions. An alternate N-protection method, of homolysine using N-benzyloxycarbonyloxy-5-norbornene-2,3-dicarboxamide, [Paquet, Can. J. Chem., 54, 73 (1976)] resulted in a low recovery (30%) of N-Z-DL-homolysine with significant polymeric by-product.

Disrupting the amino acid-Cu(II) complex followed a recently reported method [Taylor, et al., Int. J. Pept. Protein Res., 19, 158 (1982)] for the decomposition of copper(II) complex with alkaline thioacetamide (pH 8), instead of the more often used $H_2S$ and KCN [Synge, Biochem. J., 42, 99, (1948); and Zahn et al., Chem. Ber., 89, 407 (1956)]. Use of this recent method obviated the problems of prolonged heating of highly acidic solutions, colloidal CuS contamination, and the toxicity associated with $H_2S$ or KCN. The hydrolysis of thioacetamide was promoted by base to yield sulfide ions causing CuS to coprecipitate with N—Z—DL—homolysine. Under acidic conditions the CuS was removed, and the product was reprecipitated at pH 8 in high yield. Applying standard t-butoxycarbonyl acylation conditions (di-tert-butyldicarbonate in THF/water, 1:1) to N-DL-homolysine completed the synthesis of $N^\alpha$-tert-butoxycarbonyl-N-benzylcarbonyl-2,7-diaminoheptanoic acid ($N^\alpha$-t-Boc-N-Z-DL-homolysine). In a similar manner the higher homologs, 2,8-diaminooctanoic acid 8 and corresponding $N^\alpha$-t-Boc-$N^n$-Z-2,8-diaminooctanoic acid 10, were prepared. Deprotection was accomplished by standard methods.

The ease of preparation of DL-homolysine, 2,8-diaminooctanoic acid and protected derivatives, via the proposed modification of acetamidomalonic ester synthesis and subsequent protection scheme, makes it a promising general route to racemic $\alpha,\omega$-diamino acids such as ornithine, lysine and the like.

Following are examples which illustrate the process of the present invention. Temperatures are in °C., unless otherwise indicated. Melting points (mp) were determined on a Thomas Hoover melting point apparatus and are uncorrected. Elemental analyses were performed on a Perkin Elmer 240 Elemental Analyzer. NMR spectra ($^1H$) were recorded on a Nicolet Nt 360 spectrometer and are expressed as ppm downfield from TMS. Observed splittings are given in Hz. Fast atom bombardment (FAB) mass spectrometry was performed on an adapted Varian 731 spectrometer. Molecular weights (MW) were calculated using single isotope values and compared to MW implied by the observed $(M+H)^+(m/e)$. HPLC analyses were performed with a Hewlett-Packard 1084B chromatograph, a Waters C-18 column, a pH 3.2 triethylaminephosphate buffer-/acetonitrile gradient elution system and a UV detector at 210 nm. HPLC purity is reported in area-% with a sensitivity cutoff of 0.1% for injection of a 20 $\mu$l sample at 1 mg/ml. Spinco analyses were performed on a Beckman 6300 amino acid analyzer with UV detection at 570 nm using System 6300 Buffers-A,B,D,S. Samples were run directly without hydrolysis. Thin layer chromatography (TLC) was done on E. Merck silica gel plates (60F-254), and components were visualized by UV (254 nm), iodine, t-butylhypochlorite-KI reagents (for —NH—) and ninhydrin (for —$NH_2$). Systems used for TLC were:

(A) $CHCl_3/CH_3OH/H_2O$, 80:20:2;
(B) $CHCl_3$/iPrOH, 20:1;
(C) BuOH/acetic acid/$H_2O$, 4:1:1;
(D) 10% $NH_4OH/CH_3OH$;
(E) $CHCl_3/CH_3OH/H_2O$/acetic acid, 60:40:3:6; and
(F) $CHCl_3/CH_3OH/H_2O$/acetic acid, 80:20:2:1.

EXAMPLE 1

Preparation of 5-bromopentylphthalimide (3)

Phthalic anhydride (43.0 g, 0.29 mole) and 5-aminopentanol (29.9 g, 0.29 mole) in 250 ml dry toluene (dried over 4A sieves) were heated to reflux in a 120° C. oil bath with stirring for three hours. The system was equipped with a Dean-Stark trap for the azeotropic removal of water (5.3 ml). Upon TLC confirmation of complete formation of the intermediate, 5-hydroxypentylphthalimide ($R_f$=0.66 (A)), phosphorous tribromide (18.2 ml, 0.19 mole) in 20 ml dry toluene was added dropwise to the hot reaction mixture and the mixture was stirred for 1.5 hours at 100° C. After removal of an orange precipitate by filtration through a pad of Celite, the filtrate was concentrated by rotary evaporation, and the resulting oil was crystallized from absolute ethanol as white plates. Yield: 64.7 g (75.3%). Mp 59.5°–66.0° C. TLC: $R_f$=0.78 (A). MW calc. 295.10, found 295. Anal. calc. for $C_{13}H_{14}NO_2Br$: C, 52.72; H, 4.76; N, 4.73; Br, 26.98. Found: C, 53.17; H, 4.91; N, 4.62; Br, 27.14. HPLC 100%. $^1H$ NMR ($CDCl_3$) 1.50 (2H, m), 1.72 (2H, m), 1.92 (2H, m), 3.40 (2H, t, 7 Hz), 3.70 (2H, t, 7 Hz), 7.72 (2H, m) and 7.90 (2H, m) for AA'BB''system.

EXAMPLE 2

Preparation of 6-bromohexylphthalimide (4)

6-Bromohexylphthalimide was prepared in a manner similar to Example 1. Yield: 68.1 g (76%). Mp 58.5°–59.5° C. TLC: $R_f$=0.78 (A). MW calc. 309.12, found 309. Anal. calc for $C_{14}H_{16}NO_2Br$: C, 54.21; H, 5.20; N, 4.52; Br, 25.76. Found: C, 54.51; H, 5.25; N, 4.57; Br, 25.92. HPLC 97.5%. $^1H$ NMR ($CDCl_3$) 1.50 (4H, br s), 1.70 (2H, m), 1.92 (2H, m), 3.40 (2H, t, 7 Hz), 3.70 (2H, t, 7 Hz), 7.72 (2H, m) and 7.90 (2H, m) for AA'BB''system.

EXAMPLE 3

Preparation of diethyl 2-acetamido-2-(5-phthalimidopentyl)-malonate (5)

Diethyl acetamidomalonate (2.80 g, 12.9 mmole) in 10 ml dimethylformamide (dried over 4A sieves, degassed) was added dropwise over 15 minutes to a suspension of sodium hydride (515 mg of 60% NaH/oil washed free of oil with hexane, 12.9 mmole) in 10 ml DMF with external cooling to maintain reaction temperature <10° C. The reaction mixture was warmed slowly to room temperature over 45 minutes. A solution of 5-phthalimidopentyl bromide (4.24 g, 14.3 mmole) in 10 ml DMF was added in four portions at room temperature while maintaining the internal temperature <40°

C. The mixture was stirred for 24 hours until complete by TLC (product $R_f$=0.43, starting material $R_f$=0.32 (B)). Upon completion, the reaction mixture pH was adjusted to "pH 6" (pH 0–14, ColorpHast indicator strips, E. Merck, moistened) with 4N HCl/dioxane. The solvent was removed by rotary evaporation to give 9.10 g of an oil, which was purified by Still column chromatography (230–400 mesh Whatman G-60 silica gel, 320 g, CHCl$_3$ eluant). The purified adduct 5 was crystallized from ethyl acetate/cyclohexane, 1:3. Yield: 4.35 g (78%). Mp 70°–72° C. TLC: $R_f$=0.43 (B). MW calc 432.19, found 432. Anal. calc for $C_{22}H_{28}N_2O_7$: C, 61.10; H, 6.53; N, 6.48. Found: C, 60.72; H, 6.61: n, 6.12. HPLC 97.4%. $^1$H NMR (CDCl$_3$) 1.15 (2H, m), 1.25 (6H, t, 7 Hz), 1.33 (2H, br m), 1.56 (3H, s), 1.66 (4H, m), 2.05 (1H, s), 2.32 (2H, m), 3.65 (2H, t, 7 Hz), 4.25 (4H, q, 7 Hz), 7.72 (2H, m) and 7.90 (2H, m) for AA'BB"system.

EXAMPLE 4

Diethyl 2-acetamido-2-(6-phthalimidohexyl)malonate (6)

Diethyl 2-acetamido-2-(6-phthalimidohexyl)-malonate (6) was prepared in a manner similar to Example 3. Yield: 3.28 g (74%). Mp 68.5°–70.0° C. TLC: $R_f$=0.42 (B). MW calc 446.21, found 446. Anal. calc for $C_{23}H_{30}N_2O_7$: C, 61.89; H, 6.77; N, 6.27. Found: C, 62.21; H, 6.98; N, 6.67. HPLC 92%. $^1$H NMR (CDCl$_3$) 1.10 (2H, m), 1.25 (6H, t, 7 Hz), 1.34 (4H, m), 1.65 (2H, m), 2.04 (3H, s), 2.15 (1H, s), 2.30 (2H, m), 3.65 (2H, t, 7 Hz), 4.25 (4H, q, 7 Hz), 7.72 (2H, m) and 7.90 (2H, m) for AA'BB"system.

EXAMPLE 5

Preparation of 2,7-diaminoheptanoic acid monohydrochloride (DL-Homolysine-HCL) (7)

A mixture of 14.63 g (0.34 mole) the compound 5 and 6N HCl (200 ml) was heated at reflux for five hours then cooled to precipitate the phthalic acid which was removed by filtration. The filtrate was concentrated in vacuo to remove the excess HCl, and the residue was precipitated from absolute ethanol in acetone, as an oil. The oil was dissolved in 40 ml water and charged to the top of a strong acid cation exchange column, Bio Rad AG50W-X8 (3.75 cm W×48 cm L). Following a water wash of two column volumes an ammonium hydroxide gradient (0.3–0.5N) was used to elute the product. Concentration of the column effluent, pH adjustment to pH 5.8 and crystallization from water/ethanol afforded the monohydrochloride of DL-homolysine 7. Yield: 10.2 g (94%). Mp 263° C. (lit. mp 264° C. for monohydrochloride, lit mp 176° C. for monohydrochloride monohydrate). TLC: $R_f$=0.11 (C), 0.30 (D). MW calc 160.12, found 160. Anal. calc. for $C_7H_{16}N_2O_2$·HCl: C, 42.74; H, 8.20; N, 14.24; Cl, 18.02. Found: C, 42.90; H, 8.65; N, 14.17; Cl, 18.35. HPLC 96%. $^1$H NMR (D$_2$O) 1.45 (4H, m), 1.70 (2H, m), 1.88 (2H, m), 3.00 (2H, m), 3.75 (1H, t, 7 Hz). Spinco analysis: single peak with elution time equivalent to ammonia.

EXAMPLE 6

2,8-Diaminooctanoic acid monohydrochloride (8)

2,8-Diaminooctanoic acid monohydrochloride (8) was prepared in manner similar to Example 5. Yield: 1.065 g (91%). Mp 276°–277° C., monohydrochloride (lit mp 226°–229° C. for dihydrochloride). TLC: $R_f$=0.28 (D), 0.10 (C). MW calc 174.14, found 174. Anal. calc for $C_8H_{18}N_2O_2$·HCl: C, 45.60; H, 9.09. N, 13.29; Cl, 16.83. Found: C, 45.30; H, 9.29; N, 13.12; Cl, 17.11. HPLC 99%. $^1$HNMR (D$_2$O) 1.40 (6H, m), 1.68 (2H, m), 1.85 (2H, m), 3.00 (2H, t, 7 Hz), 3.75 (1H, t, 7 Hz). Spinco analysis: single peak with elution time equivalent to arginine.

EXAMPLE 7

Preparation of N$^z$-carbobenzyloxy-2,7-diaminoheptanoic acid, (N$^z$-Z-DL-homolysine) (9)

Formation of the copper-II complex of 2,7-diaminoheptanoic acid resulted from adjusting the pH of a solution of 2,7-diaminoheptanoic acid hydrochoride (1.38 g, 7.0 mmole) and CuCl$_2$2H$_2$O (597 mg, 3.5 mmole) in 30 ml water to pH 9.5 with 2.5N NaOH (3.08 ml). At 0° C., benzyl chloroformate (Z-Cl) (1.10 ml, 7.7 mmole) was added with vigorous stirring while maintaining the pH at 9.5 for 3.5 hours. The reaction was complete when the pH failed to change over 30 minutes. The solid N$^z$-Z-2,7-diaminoheptanoic acid copper-II complex was collected by filtration to give 2.54 g light blue solid (nominally 6.5 mmole). Decomposition of the copper(II) complex (1.97 g, nominally 5.0 mmole) was accomplished by suspending the blue solid in 25 ml water to which thioacetamide (620 mg, 7.5 mmole) was added. The pH was adjusted to pH 8 with 2N NaOH, and the mixture stirred for 24 hours at room temperature. The pH was brought to pH 1.6 with 2N HCl, and the precipitated CuS was removed by filtration and then washed with 5 ml 1N HCl and 2×5 ml water. The product was precipitated by adjusting the pH to 8.0 with 2N NaOH and reducing the volume in vacuo. The solid was collected by filtration, washed with water and recrystallized from HCl/NaOH to afford N-Z-2,7-diaminoheptanoic acid. Yield: 1.47 g (85% from 7). Mp 258°–259° C. TLC: $R_f$=0.33 (E). MW calc 294.16, found 294. Anal. calc for $C_{15}H_{22}N_2O_4$: C, 61.00; H, 7.51; N, 9.48. Found: C, 60.72; H, 7.58; N, 9.14. HPLC 97%. $^1$H NMR (CDCl$_3$) 1.40 (2H, m), 1.55 (2H, m), 1.70 (2H, m), 1.80 (2H, m), 3.15 (2H, m), 4.10 (1H, m), 4.30 (1H, br s), 5.05 (2H, s), 7.35 (5H, m).

EXAMPLE 8

Preparation of N$^n$-Z-2,8-diaminooctanoic acid (10)

In a manner similar to Example 7, N$^n$-Z-2,8-diaminooctanoic acid copper-II complex (1.24 g) was isolated and treated with alkaline thioacetamide to obtain N$^n$-Z-2,8-diaminooctanoic acid (10). Yield: 1.21 g (82% from 8). Mp 265°–267° C. TLC: 0.34 (E). MW calc 308.17, found 308. Anal. calc for $C_{16}H_{24}N_2O_4$; C, 62.12; H, 7.82; N, 9.05. Found:C, 61.85; H, 7.99; N, 8.92. HPLC 92%. $^1$H NMR (CDCl$_3$) 1.40 (4H, m), 1.50 (2H, m), 1.61 (2H, m), 1.78 (2H, m), 3.10 (2H, m), 4.05 (1H, m), 4.8 (1H, br s), 5.06 (2H, s), 7.35 (5H, m).

EXAMPLE 9

N$^α$-tert-Butoxycarbonyl-N$^z$-benzyloxycarbonyl-2,7-diaminoheptanoic acid (N$^α$-t-Boc-N-Z-DL-homolysine) (11)

tert-Butoxycarbonyl protection of the N$^α$-amine was carried out according to a standard procedure. To a mixture of compound 9 (4.40 g, 15.0 mmole) and diisopropylethylamine (6.74 g, 9.09 ml, 52.5 mmole), in 120 ml, 1:1 tetrahydrofuran in water, was added di-tert-butyldicarbonate (3.59 g, 16.0 mmole). The reaction was stirred at room temperature for six hours until complete by TLC (starting material 9 R$_f$=0.33, product 11 R$_f$=0.70 (F)). After removal of the THF in vacuo, the pH of the aqueous solution was adjusted to pH 2.0 and extracted with ethyl acetate (3×75 ml). The combined extracts were washed with 10% citric acid (2×20 ml) and water (3×10 ml), dried over Na$_2$SO$_4$, filtered and evaporated in vacuo to N$^\alpha$-t-boc-N$^z$-benzyloxycarbonyl-2,7-diamino heptanoic acid (N$^\alpha$-t-Boc-N-Z-DL-homolysine) 11. Yield: 5.34 g colorless oil (90%). TLC: R$_f$=0.70 (F). MW calc 394.21, found 394. Anal. calc for C$_{20}$H$_{30}$N$_2$O$_6$: C, 60.74; H, 7.65; N, 7.08. Found: C, 59.25; H, 7.64; N, 6.39. HPLC 95%. $^1$H NMR (CDCl$_3$) 1.40 (2H, m), 1.50 (9H, s), 1.55 (2H, m), 1.70 (2H, m), 1.80 (2H, m), 3.15 (2H, m), 4.10 (1H, m), 4.3 (1H, br s), 4.8 (1H, br s), 5.10 (2H, s), 7.35 (5H, m).

EXAMPLE 10

N$^\alpha$-t-Boc-N$^n$-Z-2,8-diaminooctanoic acid (12)

N$^\alpha$-t-Boc-N$^n$-Z-2,8-diaminooctanoic acid (12) was prepared from N$^n$-Z-2,8-diaminnooctanoic acid (10) in a manner similar to (11). Yield: 0.98 g (92%). TLC: one spot, R$_f$=0.68 (F). MW calc 408.23, found 408. Anal. calc for C$_{21}$H$_{32}$N$_2$O$_6$: C, 61.60; H, 7.88; N, 6.84. Found: C, 61.25; H, 7.81; N, 6.56. HPLC 93%. $^1$H NMR (CDCl$_3$) 1.40 (4H, m), 1.50 (9H, s), 1.61 (2H, m), 1.70 (2H, m), 1.78 (2H, m), 3.14 (2H, t, 7 Hz), 4.05 (1H, m), 5.06 (2H, s), 7.35 (5H, m).

What is claimed is:

1. A process for preparing α,ω-diamino acids of the formula:

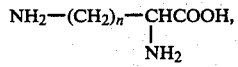

$$NH_2-(CH_2)_n-CHCOOH, \quad (I)$$
$$\quad | $$
$$\quad NH_2$$

wherein n is 3-10, which comprises:
(a) reaction of phthalic anhydride and an amino alcohol of the formula:

$$NH_2-(CH_2)_n-OH$$

in a hydrocarbon solvent, with the azeotropic removal of the water formed during the reaction;
(b) treatment of the reaction product from step "a" with PBr$_3$ or PCl$_5$ to obtain:

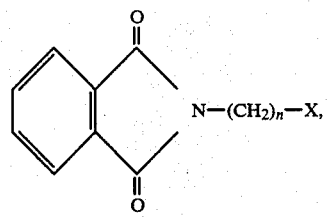

wherein X is Cl or Br;

(c) alkylating diethyl acetamidomalonate with B in the presence of sodium hydride in dimethylformamide to obtain:

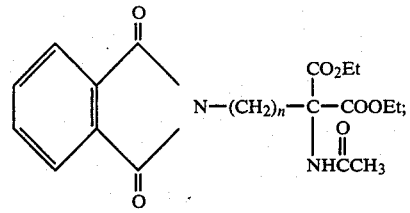

(d) hydrolyzing and decarboxylating C to obtain:

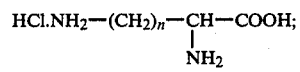

(e) chelating D with CuCl$_2$, acylating the chelate with benzylchloroformate of the formula:

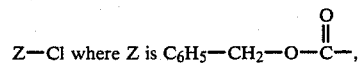

and decomposing the acylated chelate with alkaline thioacetamide of the formula:

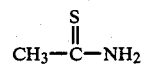

to obtain:

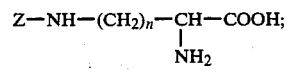

(f) acylating E to obtain the N-protected derivative of the formula:

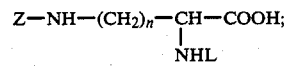

wherein L is a urethane-type protecting group selected from the group consisting of tert-butyloxycarbonyl, benzyloxycarbonyl, furfuryloxycarbonyl, and diisopropylmethyloxy carbonyl; and
(g) deprotecting F to obtain an α,ω-amino acid of formula I.

2. The process of claim 1 wherein n is 3 to 6.
3. The process of claim 1 wherein n is 3.
4. The process of claim 1 wherein n is 5.
5. The process of claim 1 wherein n is 6.
6. The process of claim 1 wherein PBr$_3$ is used in step "b".
7. The process of claim 4 wherein L in step "f" is tert-butyloxycarbonyl.

* * * * *